(12) United States Patent
Malik

(10) Patent No.: US 6,803,209 B2
(45) Date of Patent: Oct. 12, 2004

(54) PREPARATION FOR USE IN CELL CULTURE IN WHICH AN INTERFERING COMPOUND IS ABSENT OR DEPLETED

(76) Inventor: Pratap Malik, 205 Walden St. Apt. 4B, Cambridge, MA (US) 02140

( * ) Notice: Subject to any disclaimer, the term of this patent is extended or adjusted under 35 U.S.C. 154(b) by 92 days.

(21) Appl. No.: 09/779,984

(22) Filed: Feb. 9, 2001

(65) Prior Publication Data

US 2003/0054496 A1 Mar. 20, 2003

Related U.S. Application Data

(60) Provisional application No. 60/181,614, filed on Feb. 10, 2000.

(51) Int. Cl.⁷ .......................... C07K 1/22; C12P 21/00; C12P 21/08
(52) U.S. Cl. .................... 435/69.1; 435/69.5; 435/69.6; 435/70.1; 435/70.21; 435/404; 435/408; 436/548; 530/413; 530/417

(58) Field of Search .............................. 530/340.5, 413, 530/417; 435/69.6, 70.21, 404, 408, 69.1, 69.5, 70.1; 436/548

(56) References Cited

U.S. PATENT DOCUMENTS 5,019,270 A  *  5/1991  Afeyan et al. .............. 210/656

* cited by examiner

Primary Examiner—David Saunders
(74) Attorney, Agent, or Firm—Kriegsman & Kriegsman

(57) ABSTRACT

A cell culture preparation and methods are provided which are suitable for production in cells of a first protein in a class of proteins where the medium is deficient in a second protein in a related class, where the second protein is normally present in the serum and capable of interfering with the purification of the first compound.

23 Claims, 1 Drawing Sheet

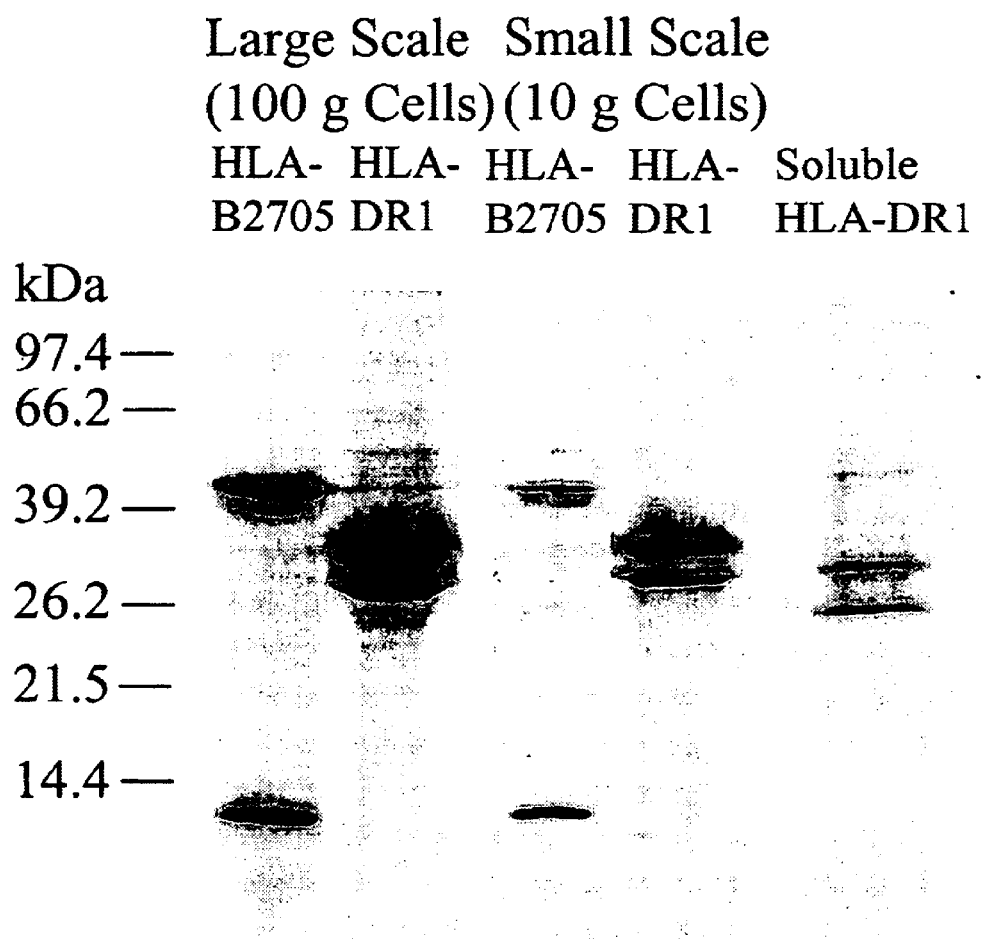
Fig. 1. SDS-PAGE analysis of purified HLA-B2705 and HLA-DR1 protein molecules from 100 g cells (large scale) and 10 g cells (small scale) and from cell supernatant of soluble HLA–DR1 producing cells. The gel was stained with Coomassie blue.

PREPARATION FOR USE IN CELL CULTURE IN WHICH AN INTERFERING COMPOUND IS ABSENT OR DEPLETED

CROSS REFERENCE

This application gains priority from provisional application Ser. No. 60/181,614 filed Feb. 10, 2000 herein incorporated by reference.

STATEMENT REGARDING FEDERALLY SPONSORED RESEARCH OR DEVELOPMENT

The invention was sponsored by NIH grant No. AI45198 and the government has certain rights to this invention.

TECHNICAL DESCRIPTION

A serum containing preparation is provided that is depleted in or devoid of interfering proteins, the proteins being otherwise present in the serum and methods for preparing the same. Methods of purifying cell culture product is further provided.

BACKGROUND TO THE INVENTION

Preparation of proteins using eukaryotic cell culture techniques is a well established methodology. Purification of proteins manufactured in eukaryotic cell cultures that rely on serum enriched media is problematic in part because the serum contains related proteins. These proteins are bovine proteins if the serum is derived from a cow or calf or bovine fetus. Alternatively, the proteins may be rabbit, horse or other animal proteins where these animals are the source of the serum. It is desirable to avoid a step or several steps of purification of the desired protein away from related contaminating proteins derived from the serum.

One approach to this problem is to avoid the use of serum in the medium in which the cells are cultured. This is often problematic because cells rely on the rich source of nutrients provided by serum. Alternatively, the serum may be treated prior to sterilization and use by means of affinity chromatography techniques to remove the contaminating proteins. The problem here is that serum is very viscous and the capacity of the affinity chromatography column is small. Therefore affinity chromatography of serum is costly and time consuming.

As the requirement for therapeutic molecules and research reagents increases, the need for rapid methods for producing large amount of serum containing medium that is devoid of interfering proteins increases.

An example of a group of proteins that is of interest in bio-diagnostics, therapeutics and as research reagents and is prepared in cell culture are the antibodies and the Fc chimeric proteins that have the Fc part of an antibody fused with another protein. It is desirable to purify this group of proteins as a product of tissue culture. One of the most commonly used procedures for purification of antibodies is based on immunoaffinity purification using protein A or G. The original protocols use high porosity cross-linked carbohydrate supports for example, Sepharose. Since these supports are compressible, the purification using these supports done at slow flow rates. These slow flow rates are problematic and to speed up the rate of purification, newer chromatography technologies have recently been developed which permit much higher flow rates in chromatographic processes, for example, Perfusion Chromatography (PE Biosystems), HyperDiffusion Chromatography (BioSepra, Inc.) etc. Perfusion chromatography involves the flow of liquid through a non-compressible porous chromatographic particle POROS® Media, PE Biosystems) and the maximum flow rate is limited by the maximum pressure the chromatography system can withstand. It has become extremely desirable to produce antibody molecules and the Fc-fusion proteins in cell culture media that are devoid of bovine antibodies that may interfere with the purification of the desired protein molecules.

SUMMARY

The embodiments of the invention provide a novel culture medium and method of purifying proteins.

In a preferred embodiment, a cell culture medium is provided that includes a mixture of a serum supplement and a culture medium, wherein the mixture is deficient in a compound normally present in the serum supplement.

In a preferred embodiment, a method of preparing a culture medium containing serum, suitable for production in cells of a first protein in a class of proteins is provided where the medium being deficient in a second protein in a related class, the second protein normally present in the serum and capable of interfering with either the growth of the cells or the purification of the first compound; the steps of the method comprising; selecting the culture medium containing serum; subjecting the mixture to a chromatography step so as to provide an eluant, the eluant being deficient in the interfering second protein; and utilizing the eluant as a culture medium for production of the first protein by cells.

In a preferred embodiment, a method for obtaining a purified cell culture product; is provided that includes the steps of selecting a serum supplement and a nutrient medium suitable for cell culture; combining the serum supplement with the nutrient medium to form a mixture; subjecting the mixture to an affinity chromatography step so as to remove a compound capable of interfering with the preparation of the cell culture product, the chromatography step providing a flow through, and obtaining the purified cell culture product from cells grown or maintained in the flow through.

In further embodiments of the invention, affinity chromatography includes protein A and protein G column and more particularly perfusion column. Cell culture products include but are not limited to monoclonal antibodies, Fc-fusion proteins (Fc-Chimeric proteins), MHC proteins, growth factors, cytokines, hormones and serum albumin. Proteins to be removed from serum include but are not limited to antibodies, proteins or protein fragments or peptides capable of binding MHC, growth factors, cytokines serum albumin and pathogenic material.

LIST OF FIGURES

FIG. 1 shows an SDS-PAGE analysis of purified HLA-DR1 protein molecules from cell supernatant of soluble HLA-DR1 producing cells. The gel was stained with coomassie blue.

DETAILED DESCRIPTION OF THE INVENTION

The present invention relates to removal of components from serum containing media for the use in cell culture including the removal of antibodies by affinity purification.

Serum is an essential component of most cell culture media. However serum may contain components that may interfere with either cell growth or with the proteins that may be obtained from a particular cell culture or its supernatant. For monoclonal antibody production from hybridoma cell supernatant, the cell culture supernatant should be free of serum antibodies. To achieve this, cells must be grown up in medium which is either serum free, or has a serum substitute or has a serum supplement from which the serum antibody has previously been depleted. There are various ways that serum could be depleted of antibodies e.g. Cohn fractionation process, in which ethanol is used to precipitate gamma globulin or by contacting the serum with protein G or protein A (Zeng et al., 1997) (Aybay, and Imir, T: (2000). The ethanol precipitation is non-specific and may remove components important for the growth of cells. Depleting serum of antibodies by contacting with protein G or protein A is a very slow, inefficient and costly process which requires incubation days, or slow speed passage overnight with several repetitions of passages.

The present invention overcomes the drawbacks of the prior art by providing means of generating a serum containing medium (as opposed to just the serum) or a serum preparation that has been depleted in specific components and provides a means of improved efficiency and speed of the depletion. The advent of newer chromatography technologies which permit superior flow advantages for example Perfusion Chromatography (PE Biosystems), HyperDiffusion Chromatography (BioSepra, Inc) etc, have made it possible to pass large amounts of material at very high flow rates in chromatographic processes. In general, the less viscous serum preparations, including serum containing cell culture medium, are more amenable to purification at higher flow rates (600 ml/hr to 2400 ml/hr or even higher) than the pure serum. This process is also amenable to scale up to any size. These factors make this process commercially viable and attractive. Affinity chromatography is applied on serum containing medium to remove/deplete specific components from the medium without adversely affecting the growth ability of the medium. The medium depleted in specific components may be sterilized and used in cell culture.

Here a novel methodology is described where bovine IgG may be very rapidly removed from serum preparations for use in cell culture using immunoaffinity columns in Perfusion Chromatography (Afeyan et al., 1991). Perfusion chromatography involves the flow of liquid through a non-compressible porous chromatographic particle (POROS® Media, PerSeptive Biosystems) with 6000–8000 A pores which transect the particle. These through pores allow very high flow rates and enable rapid loading, washing cleaning and elution of the column. We have applied perfusion affinity-chromatography using the BioCAD® Workstation.

Development and modernization of the methodologies of purification and isolation of protein molecules are needed to keep pace with the state-of-the-art technologies for protein purification and peptide analyses. The methodology described above serves as a model for the rapid purification of all other MHC class I and class II molecules. The speed of purification reduces the handling time of the serum preparation and ensures an improved cost effectiveness and quality. Such a technological advance is fundamental to a sophisticated study of the immune response to foreign antigens, self-tolerance and autoimmunity and to the development of peptide vaccines based on the use of MHC-restricted epitopes for anti-tumor and anti-viral immunotherapy.

Pure monoclonal antibodies, humanized antibodies and Fc-fusion (chimeric) proteins are finding increased use in therapeutics and biomedical research. One of the more commercially popular ways is to produce antibodies as cell culture supernatant followed by affinity purification. Most antibody producing cells require serum-containing medium. This medium preparation has antibodies from the serum component. The spent medium thus has the antibody of interest and the previously present antibodies. The prior art technique of separating an antibody of interest from the previously present antibodies is expensive and technologically involved. However, using this invention, a medium free of antibodies could be generated for the culture of antibody producing cells in a cost efficient manner.

This process can rapidly achieve isolation or removal of particular components that may be present in the serum. For example, a serum preparation that is amenable for rapid purification can be used for removal or isolation of antibodies to particular pathogen in the serum by passage of the serum preparation over an affinity column with the pathogen antigen(s) immobilized onto column matrix.

EXAMPLES

Example 1

A Model System for Removal of Serum Antibodies from Media Containing Serum Prior to Preparation of Monoclonal Antibodies in Hybridoma Cells in Cell Culture Medium.

Typically one liter RPMI 1640 cell culture medium containing 10% heat inactivated fetal bovine serum (Hyclone) was run on a 7.5×300 mm POROS® 20G (protein G coupled to POROS® 20) column at 600 ml/hr. The column was washed with 5 column volume of 2% acetic acid. The eluted antibody was immediately neutralized with 1M Tris base and the column equilibrated with PBS. The flow through serum containing medium was practically depleted of the entire bovine IgG as checked by ELISA. It was then supplemented with 2 mM glutamine (Gibco BRL), 50 U/ml penicillin (Gibco BRL) and 50 g/ml streptomycin (Gibco BRL), filter sterilized.

Production and Purification of Monoclonal Antibodies

The above medium was used to grow the monoclonal antibody producing hybridoma cell line ME1 (an anti-HLA-B27 mouse IgG1 monoclonal antibody (Ellis et al., 1982), LB3.1 (an anti-HLA-DR, mouse IgG2b monoclonal antibody (Gorga et al., 1986) and 4418 (an anti NKp44, mouse IgG1 monoclonal antibody). The LB3.1 monoclonal antibody was purified by running the cell culture supernatant on POROS® 20A (protein A coupled POROS® 20 medium) and the ME1 and 4418 monoclonal antibodies were purified by running the cell culture supernatant on POROS® 20G protein G coupled to POROS® 20 medium used for IgG1 antibodies) column using a BioCAD™ Workstation for perfusion chromatography (PerSeptive Biosystems). Typically 1–2 liters of cell culture supernatant was filtered through 0.2 micron filter and run on a POROS® 20A or a POROS® 20G column. The column was washed with 5 column volume of 2% acetic acid. The eluted antibody was immediately neutralized with 1M Tris base and the column equilibrated with PBS.

Production and Purification of a Fc Fusion Protein Exemplified by NKp46-Ig

Transiently transfected COS cells with NK-46Ig gene construct were grown in the IgG free medium. The supernatant from these cells was run on POROS® 20G column as above and the pure NKp46-Ig fusion protein purified.

Preparation of Immunoaffinity Columns for Removal of Serum Proteins from Serum Containing Media Prior to Preparation of Cell Culture Products Typically 10–20 mg of the purified monoclonal antibody in PBS was coupled to one ml of POROS® 20 AL medium (P0ROS® 20 medium activated with the aldehyde group)

(PE Biosystems). To about 5–10 mg/ml of antibody in PBS was added ½ volume of High Salt Buffer Solution (1.5 M sodium sulfate in 100 mM sodium phosphate 7.4). This was made 5–10 mg/ml in NaCNBH3 (Sigma). To this was added the appropriate amount of POROS® 20 AL (generally slightly more than the desired column volume) and the solution was made to 0.9–1.1 M in Na2SO4 by the addition of High Salt Buffer Solution. The final concentration of the antibody was between 1–2 mg/ml. The reaction was carried out overnight by gentle shaking. The media was filtered in a 10–20 m sintered glass funnel and resuspended in 50–100 ml of Capping Buffer (5 g/l NaCNBH3 in 0.2 M Tris, pH 7.2) for about one hour. The media was then washed with PBS and packed in a column. Columns ranging from 4.4 ml (100×7.5 mm) to 13.25 ml (300×7.5 mm) PEEK (polyetheretherketone) columns (Alltech) were packed under the conditions specified by the manufacturer. A pre-clearing column using normal mouse serum (NMS) was also prepared and used to remove proteins that adhered non-specifically to IgG.

Purification of a Protein Exemplified by HLA-DR1 as a Model

Soluble HLA-DR1 molecules were expressed in Drosophila S2 cells as described (Stern and Wiley, 1992; Kalandadze et al., 1996; Dessen et al., 1997). Cells were grown in roller bottles in ExCell 401 medium (JRH Biosciences supplemented with 0–5% fetal bovine serum (Sigma) at 26° C. Cells were harvested 4–5 days after induction by 1 mM $CuSO_4$. The supernatant was collected by centrifugation, filtered through 0.2 m filtration unit (Corning). The filtered supernatant was passed through the series of columns consisting of POROS® 20 AL-NMS, POROS® 20A, and POROS® 20 AL-LB3.1. The protein was eluted by passing 50 mM glycine pH 11.5 solution at 2–5 ml/min through POROS® 20 AL-LB3.1 column. The column was washed with several volumes of PBS and the eluted protein was immediately neutralized with 2M Tris-HCl pH 6.5. The POROS® 20 AL-NMS and POROS® 20A were treated as above. Typically 1 liter of cell supernatant was used with columns of 13.25 ml.

Soluble HLA-DR1 molecules were expressed in Drosophila S2 cells as described (Stern and Wiley, 1992) Kalandadze et al., 1996; Dessen et al., 1997). Cells were grown in roller bottles in ExCell 401 medium (JRH Biosciences) supplemented with 0–5% fetal bovine serum (Sigma at 26° C. Cells were harvested 4–5 days after induction by 1 MM CuSO4. The supernatant was collected by centrifugation, filtered through 0.2 m filtration unit (Corning). The filtered supernatant was passed through the series of columns consisting of POROS® 20 AL-NMS, POROS® 20 A, POROS® 20 AL-LB3.1. The protein was eluted by passing 50 mM glycine pH 11.5 solution at 2–5 ml/min through POROS® 20 AL-LB3.1 column. The column was washing with several volumes of PBS and the eluted protein was immediately neutralized with 2 M tris-HCl pH 6.5. The POROS® 20 AL-NMS and POROS® 20 A were treated as above. Typically 1 liter of cell supernatant was used with columns of 13.25 ml.

Table 1
Yields of MHC Proteins

TABLE 1

Yields of MHC proteins

| | Approximate yield Small scale (10 g cells) | Large scale (100 g cells) |
|---|---|---|
| HLA-B2705 | 0.5–1 mg | 7–10 mg |
| HLA-DR1 | 5–10 mg | 50–75 mg |

Table 2
Pooled Sequencing of HLA-B2705 Eluted Peptides

The yield in pmol of amino acid residues in each sequencing cycle of Edman degradation is shown. The yields for the expected motif vix arginine at position 2 and tyrosine, phenylalanine or leucine at position 9 are shown in bold.

TABLE 2

Pooled sequencing of HLA-B2705 eluted peptides
The yield in pmol of amino acid residues in each sequencing cycle of Edman degradation is shown. The yields for the expected motif vix. arginine at position 2 and tyrosine, phenylalanine or leucine at position 9 are shown in bold.

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| N | 3 | 2 | 13 | 12 | 7 | 9 | 9 | 22 | 4 | 2 | 2 | 1 | 1 | 1 | 1 |
| S | 7 | 5 | 5 | 8 | 6 | 7 | 5 | 6 | 3 | 2 | 5 | 3 | 2 | 2 | 1 |
| Q | 1 | 21 | 10 | 29 | 13 | 14 | 8 | 18 | 9 | 4 | 2 | 2 | 2 | 2 | 1 |
| T | 5 | 3 | 7 | 22 | 20 | 12 | 16 | 12 | 5 | 5 | 3 | 2 | 2 | 2 | 2 |
| G | 32 | 8 | 8 | 27 | 33 | 14 | 11 | 14 | 11 | 6 | 4 | 3 | 3 | 3 | 3 |
| E | 3 | 7 | 6 | 26 | 20 | 17 | 14 | 21 | 8 | 5 | 3 | 3 | 3 | 3 | 3 |
| H | 3 | 2 | 5 | 4 | 4 | 4 | 4 | 5 | 4 | 3 | 2 | 1 | 4 | 4 | 3 |
| A | 34 | 12 | 12 | 16 | 14 | 26 | 15 | 17 | 8 | 5 | 5 | 4 | 3 | 3 | 6 |
| R | 94 | 285 | 83 | 33 | 21 | 20 | 15 | 21 | 18 | 15 | 10 | 14 | 9 | 8 | 5 |
| Y | 7 | 2 | 21 | 7 | 10 | 7 | 12 | 7 | 11 | 19 | 8 | 4 | 3 | 2 | 2 |
| P | 6 | 5 | 17 | 13 | 21 | 19 | 14 | 8 | 5 | 3 | 3 | 2 | 2 | 6 | 8 |
| M | 3 | 4 | 8 | 5 | 6 | 2 | 3 | 2 | 7 | 3 | 2 | 1 | 1 | 1 | 0 |
| V | 7 | 7 | 15 | 6 | 14 | 16 | 17 | 11 | 15 | 7 | 4 | 4 | 3 | 2 | 2 |
| F | 11 | 4 | 43 | 9 | 12 | 8 | 16 | 8 | 17 | 8 | 4 | 2 | 2 | 2 | 1 |
| I | 15 | 3 | 12 | 3 | 6 | 6 | 10 | 4 | 4 | 2 | 1 | 1 | 1 | 1 | 0 |
| K | 14 | 2 | 9 | 12 | 10 | 14 | 6 | 7 | 13 | 5 | 3 | 1 | 1 | 1 | 1 |
| L | 5 | 6 | 32 | 14 | 16 | 14 | 24 | 13 | 34 | 10 | 5 | 3 | 2 | 2 | 2 |
| W | 1 | 0 | 8 | 3 | 2 | 1 | 3 | 1 | 1 | 1 | 0 | 0 | 0 | 0 | 0 |
| D | 5 | 4 | 7 | 27 | 16 | 11 | 0 | 8 | 5 | 4 | 3 | 3 | 3 | 2 | 2 |

What is claimed is:

1. A method of preparing a culture medium containing serum suitable for production in cells of a first protein in a class of proteins, the culture medium being deficient in a second protein in a related class, the second protein normally present in the serum and capable of interfering with the purification of the first protein, the steps of the method comprising:

(A) selecting a culture medium containing serum;

(B) subjecting the culture medium containing serum to an affinity chromatography step so as to provide a flow through, the flow through being deficient in the interfering second protein, wherein said affinity chromatography step is perfusion chromatography; and (C) utilizing the flow through as a culture medium containing serum deficient in said second protein for production of the first protein by cells.

2. A method according to claim 1, wherein step (b) further comprises completing the affinity chromatography step within 24 hours.

3. A method according to claim 1, wherein step (b) further comprises completing the affinity chromatography step within 12 hours.

4. A method according to claim 1, wherein the chromatography step includes a chromatography column containing protein G.

5. A method according to claim 1, wherein the chromatography step includes a chromatography column containing protein A.

6. A method according to claim 1, wherein the chromatography step includes subjecting the culture medium containing serum to a perfusion chromatography column having a second protein binding ligand attached thereto.

7. A method according to claim 1, wherein step (c) further comprises, the step of sterilizing the culture medium containing serum deficient in said second protein.

8. A method according to claim 1, wherein the first protein is a monoclonal antibody and the second protein is a polyclonal serum antibody.

9. A method according to claim 1, wherein the first protein is a cytokine and the second protein is a cytokine.

10. A method for obtaining a purified cell culture product comprising:

(A) selecting a serum supplement and a nutrient medium suitable for cell culture;

(B) combining the serum supplement with the nutrient medium to form a mixture;

(C) subjecting the mixture to a chromatography step so as to remove a compound capable of interfering with the preparation of the cell culture product, the chromatography step comprising perfusion chromatography and providing an eluant, and (D) obtaining the purified cell culture product from cells grown or maintained in the eluant.

11. A method according to claim 10, wherein the chromatography step includes a chromatography column containing protein G.

12. A method according to claim 10, wherein the chromatography step includes a chromatography column containing protein A.

13. A method according to claim 10, wherein the chromatography step includes subjecting the mixture to a perfusion chromatography column having a compound binding ligand attached thereto.

14. A method according to claim 10, wherein step (c) further comprises the step of sterilizing the eluant.

15. A method according to claim 10, wherein the cell culture product is a monoclonal antibody.

16. A method according to claim 10, wherein the cell culture product is a MHC protein.

17. A method according to claim 10, wherein the cell culture product is a cytokine.

18. A method according to claim 10, wherein the cell culture product is a growth factor.

19. A method according to claim 10, wherein the compound is a polyclonal serum antibody.

20. A method according to claim 10, wherein the compound is an MHC binding protein or protein fragment.

21. A method according to claim 10, wherein the compound is a cytokine.

22. A method according to claim 10, wherein the compound is a growth factor.

23. The method as claimed in claim 10, wherein the serum supplement concentration is the nutrient medium is 10% respectively.

* * * * *